United States Patent [19]
Bailey et al.

[11] Patent Number: 6,008,228
[45] Date of Patent: *Dec. 28, 1999

[54] PHARMACEUTICAL COMPOSITIONS CONTAINING PROTEINASE INHIBITORS

[75] Inventors: Carole Anne Bailey, Warren, N.J.; Josephine Christine Ferdinando, Chippenham, United Kingdom; Navnit Shah, Clifton, N.J.

[73] Assignee: Hoffman-La Roche Inc., Nutley, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/616,233

[22] Filed: May 7, 1996

Related U.S. Application Data

[63] Continuation-in-part of application No. 08/468,493, Jun. 6, 1995, abandoned.

[51] Int. Cl.[6] .......................... A01N 43/42; A01N 37/00
[52] U.S. Cl. .............................. 514/307; 514/558
[58] Field of Search ..................... 514/307, 558

[56] References Cited

U.S. PATENT DOCUMENTS

| | | | |
|---|---|---|---|
| 4,997,851 | 3/1991 | Isaacs et al. | 514/558 |
| 5,114,957 | 5/1992 | Hendler et al. | 514/356 |
| 5,120,710 | 6/1992 | Liedtke | 514/3 |
| 5,157,041 | 10/1992 | Handa et al. | 514/307 |
| 5,196,438 | 3/1993 | Martin et al. | 514/311 |
| 5,318,781 | 6/1994 | Shah et al. | 514/455 |
| 5,354,866 | 10/1994 | Kempf et al. | 546/265 |
| 5,444,041 | 8/1995 | Owen et al. | 514/2 |
| 5,538,997 | 7/1996 | Billich et al. | 514/510 |

FOREIGN PATENT DOCUMENTS

| | | | |
|---|---|---|---|
| 2 108 934 | 10/1993 | Canada | A61K 37/64 |
| 448 091 | 3/1991 | European Pat. Off. | A61K 47/14 |
| 490 667 | 11/1991 | European Pat. Off. | A61K 37/02 |
| 539 319 | 6/1992 | European Pat. Off. | A61K 37/02 |
| 526 009 | 7/1992 | European Pat. Off. | A61K 31/33 |
| 587 311 | 8/1993 | European Pat. Off. | A61K 37/64 |
| 594 540 | 10/1993 | European Pat. Off. | A61K 37/64 |
| 93/01828 | 7/1992 | WIPO | A61K 37/02 |
| 93/04043 | 3/1993 | WIPO | C07D 215/48 |
| 94/08603 | 4/1994 | WIPO | A61K 37/00 |
| 94/08605 | 4/1994 | WIPO | A61K 37/00 |
| 95/00152 | 1/1995 | WIPO | A61K 31/725 |
| 95/07696 | 3/1995 | WIPO | A61K 31/425 |

OTHER PUBLICATIONS

Alteri, El., et al., *Antimicrob. Agents Chemother.*, 37(10), 2087 (1993).
Fässler, A., et al., *Bioorg. Med. Chem. Letters*, 3(12), 2837 (1993).
Ghosh, Arun K., et al., *J. Med. Chem.*, 36, 2300–2310 (1993).
Lang, M., et al., *Arch. Pharm. (Weinheim)*, 326, 921–924 (1993).
Overton, H. A., et al., *Virology*, 179, 508–511 (1990).
Phylip, L. H., et al., *FEBS Letters*, 314(3), 449–454 (1992).
Roberts, N. A., et al., *Science*, 248, 358–361 (1990).
Tucker, T. J., et al., *J. Med. Chem.*, 35, 2525–2533 (1992).

*Primary Examiner*—Russell Travers
*Attorney, Agent, or Firm*—George W. Johnston; Patricia S. Rocha-Tramaloni; Eileen M. Ebel

[57] ABSTRACT

Compositions which increase the bioavailability of proteinase inhibitors are disclosed. Compositions which include a pharmaceutically acceptable carrier comprising monoglycerides of medium chain-fatty acids are preferred. Preferred medium chain fatty acid glycerides include monoglycerides of saturated $C_6$ to $C_{12}$ fatty acids, preferably $C_8$ to $C_{10}$ fatty acids The pharmaceutically acceptable carrier preferably has an acid value of less than or equal to about 2.5. Preferably, the ratio of monoglycerides of medium chain fatty acid to the proteinase inhibitor is about at least 1.5.

25 Claims, No Drawings

PHARMACEUTICAL COMPOSITIONS CONTAINING PROTEINASE INHIBITORS

CROSS-REFERENCE TO RELATED APPLICATION

This application is a continuation-in-part application of Ser. No. 08/468,493 now abandoned, filed Jun. 6, 1995.

BACKGROUND OF THE INVENTION

1. Field of the Invention

The present invention is related to pharmaceutical compositions which increase the bioavailability of the proteinase inhibitors.

2. Description

It is well known in the art that a wide range of diseases are caused by retroviruses.

As far as is known at the present, AIDS is a disease of the immune system caused by the retrovirus HIV (Human Immunodeficiency Virus). According to estimates by the World Health Organization, the disease, which affects about 10 million people, is continuing to spread and in virtually all cases results in the death of the patient.

Retroviruses HIV-1 and HIV-2 have been identified as a cause of the disease and they have been characterized by molecular biology.

Retroviral protease is a proteolytic enzyme that, owing to an aspartate residue in the active center, is regarded as an aspartate protease and participates in the maturation of new infectious virions in infected cells in the reproductive cycle of a number of retroviruses.

For example, HIV-1 and HIV-2 each have in their genome a region that codes for a "gag-protease". That "gag-protease" is responsible for the correct proteolytic cleavage of the precursor proteins that are produced from the genome regions coding for the "Group Specific Antigens" (gag). During the cleavage, the structural proteins of the virus core are liberated. The "gag-protease" itself is a component of a precursor protein encoded by the pol-genome region of HIV-1 and HIV-2, which protein also contains the regions for the "reverse transcriptase" and the "integrase" and is thought to be cleaved by autoproteolysis.

The "gag-protease" cleaves the major core protein p24 of HIV-1 and HIV-2 preferentially N-terminally of proline residues, for example in the divalent residues Phe-Pro, Leu-Pro, or Tyr-Pro. It is a protease having a catalytically active aspartate residue in the active center, a so-called aspartate protease.

As used herein, proteinase inhibitor refers to those compounds which inhibit aspartate proteases of viral origin and which are useful in the prophylaxis or treatment of viral infections caused by retroviruses, such as HIV, in mammals, both human and non-human. Details of the design of such proteinase inhibitors can be found, for example, in Roberts, N. A., et al., *Science*, 248, 358 (Apr. 20, 1990); Overton, H. A., et al., *Virology*, 179, 508 (1990); Tucker, T. J., et al., *J. Med. Chem.*, 35, 2525 (1992); and Phylip, L. H., et al., *FEBS Letters*, 314, 449 (1992).

Because of the hydrophobic and/or lipophilic character of proteinase inhibitors, pharmaceutical formulations thereof with conventional solid or liquid pharmaceutical excipients tend to have disadvantages. For example the proteinase inhibitor may not be satisfactorily absorbed. Among the inherent factors known to affect absorption are the method of manufacture or method of compounding; the particle size and crystal form or polymorph of the drug substance; and the diluents and excipients used in formulating the dosage form, including carriers, fillers, binders, disintegrating agents, lubricants, coatings, solvents, suspending agents, and dyes.

A requirement for therapeutic effectiveness in vivo is the achievement of good bioavailability, for example good absorptive capacity and/or a high blood level, also in the case of enteral, such as oral, administration, in order to obtain sufficiently high concentrations in the infected cells and/or good distribution within a host in need of treatment.

An additional requirement is that the unit dosage form have good stability or shelf life so that it can be stored conveniently (e.g., no refrigeration, i.e., at room temperature (about 20° C.) for a long period of time (e.g., about two years).

While there are many known proposals to alleviate or overcome problems of this type, it has been found that many of these proposals are inadequate in the area of the proteinase inhibitors. It has, however, surprisingly been found that certain classes of glycerides used as carrier components of formulation do assist in alleviating these inadequacies. In particular, they enable achievement of better absorption and thus enhanced bioavailability and have good stability or shelf life over a long period of time.

SUMMARY OF THE INVENTION

The present invention accordingly provides a pharmaceutical composition, preferably in unit dose, comprising (a) a therapeutically effective amount of a proteinase inhibitor, its pharmaceutically acceptable salts or esters (including their salts); and (b) a carrier containing a monoglyceride of $C_8$–$C_{10}$ medium chain fatty acids. The amount of the monoglyceride in the pharmaceutically acceptable carrier of component (b) is at least sufficient to dissolve the proteinase inhibitor.

Preferably, the ratio of monoglyceride of component (b) to component (a) is at least about 1.5, more preferably at least about 2.0, further preferably at least from about 2.5 to about 3.5, and most preferably at least about 3. Preferably, component (b) has a maximum acid value of about 2.5, more preferably less than or equal to about 0.5, more preferably less than or equal to about 0.26, and further preferably less than or equal to about 0.1 and even more preferably less than or equal to about 0.04.

The medium chain fatty acid glycerides can also be partially ethoxylated with polyethylene glycol of molecular weight of from about 300 to about 500, which is equivalent to about six to about eight moles of ethylene oxide.

Mixtures of the monoglyceride of $C_8$–$C_{10}$ medium chain fatty acids and the partially ethoxylated medium chain fatty acid glycerides can also be contemplated.

In particular, the proteinase inhibitor is N-tert.-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide, its pharmaceutically acceptable salts, or esters (including salts thereof).

DETAILED DESCRIPTION OF THE INVENTION

The present invention accordingly provides a pharmaceutical composition, preferably in unit dose, comprising (a) a therapeutically effective amount of a proteinase inhibitor, its pharmaceutically acceptable salts or esters (including their salts); and (b) a carrier containing a monoglyceride of $C_8$–$C_{10}$ medium chain fatty acids. The amount of the monoglyceride in the pharmaceutically acceptable carrier of component (b) is present in an amount sufficient to dissolve or solubilize the proteinase inhibitor. Preferably the ratio of monoglyceride (b) to (a) is at least about 1.5. A skilled artisan would be able to determine the amount of monoglyceride that is needed to dissolve the proteinase inhibitor in accordance with the present invention through conventional techniques.

Of particular interest are the following proteinase inhibitors, as well as their pharmaceutically acceptable salts or esters:

N-tert.-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide, and N-tert.-butyl-decahydro-2[2(R)-hydroxy-4-phenyl-3(S)-[[N-benzyloxycarbonyl)-L-asparaginyl]-amino]butyl]-(4aS,8aS)-isoquinoline-3(S)-carboxamide, which are described in U.S. Pat. No. 5,196,438, the contents of which are expressly incorporated herein by reference. In additionally, the esters and the salts thereof of the above compounds are also of interest.

Additionally, the following proteinase inhibitors, as well as their pharmaceutically acceptable salts, are of interest:

$N^2$-[3(S)-[[N-(benzyloxycarbonyl)-L-asparaginyl]amino]-2(R or S)-hydroxy-4-phenylbutyl]-$N^1$-tert.-butyl-L-prolinamide, $N^2$-[3(S)-[[N-(benzyloxycarbonyl)-L-asparaginyl]amino]-2(R or S)-hydroxy-4-phenylbutyl]-$N^1$-isobutyl-L-prolinamide, $N^2$-[3(S)-[[N-(benzyloxycarbonyl)-L-asparaginyl]amino]-2(R)-hydroxy-4-phenylbutyl]-$N^1$-tert.-butyl-4(R)-thiazolidinecarboxamide, N-tert.-butyl-1-[2(R)-hydroxy-4-phenyl-3(S)-[[N-(2-quinolylcarbonyl)-L-asparaginyl]amino]butyl]-2(S)-piperdinecarboxamide, 1-[3(S)-[[N-(benzyloxycarbonyl)-L-asparaginyl]amino]-2(R)-hydroxy-4-phenylbutyl]-N-tert.-butyl-octahydro-(3aS,6aS)-cyclopenta[b]pyrrole-2(S)-carboxamide, 1-[3(S)-[[N-(benzyloxycarbonyl)-L-asparaginyl]amino]-2(R)-hydroxy-4-phenylbutyl]-N-tert.-butyl-2(S)-piperidinecarboxamide, 2-[3(S)-[[N-(benzyloxycarbonyl)-L-asparaginyl]amino]-2(R)-hydroxy-4-phenylbutyl]-N-tert.-butyl-1,2,3,4-tetrahydropyrido[3,4-b]indole-1-carboxamide, N-tert.-butyl-3-[2(R)-hydroxy-3(S)-[[N-(2-naphthoyl)-L-asparaginyl]amino]-4-phenylbutyl]-4(R)-thiazolidinecarboxamide, $N^1$-tert.-butyl-$N^2$-[2(R)-hydroxy-phenyl-3(S)-[[N-(2-quinolylcarbonyl)-L-asparaginyl]amino]butyl]-L-prolinamide-$N^2$-oxide, 1-[3(S)-[[N-(benzyloxycarbonyl)-3-cyano-L-alanyl]amino-2(R)-hydroxy-4-phenylbutyl]-N-tert.-butyl-2(S)-piperdinecarboxamide, 1-[3-(S)-[[N-(benzyloxycarbonyl)-L-asparaginyl]amino]-2(R)-hydroxy-4-phenylbutyl]-4-(tert.butoxycarbonyl)-N-tert.-butyl-2(R or S)-piperazinecarboxamide, 1-[3(S)-[[N-(benzyloxycarbonyl)-3-cyano-L-alanyl]amino]-2(R)-hydroxy-4-phenylbutyl]-4-(tert.butoxycarbonyl)-N-tert.-butyl-2(R or S)-piperazinecarboxamide, $N^2$-[3(S)-[[N-(benzyloxycarbonyl)-L-asparaginyl]amino]-2(R)-hydroxy-4-phenybutyl]-4(R)-(tert.butoxyformamido)-$N^1$-tert.butyl-L-prolinamide, 1-[3(S)-[[N-(3-benzyloxy-2-naphthoyl)-L-asparaginyl]amino]-2(R)-hydroxy-4-phenylbutyl]-N-tert.-butyl-2(S)-piperidinecarboxamide, N-tert.-butyl-1-[2(R)-hydroxy-4-phenyl-3(S)-[[N-(2-quinolylcarbonyl)-L-asparaginyl]amino]butyl]-2-piperidinecarboxamide 1-oxide, N-tert.-butyl-1-[3(S)-[[N-(3-hydroxy-2-naphthoyl)-L-asparaginyl]amino]-2(R)-hydroxy-4-phenylbutyl]-2(S)-piperidinecarboxamide, trans-2-[3(S)-[[N-(benzyloxycarbonyl)-L-asparaginyl]amino]-2(R)-hydroxy-4-phenylbutyl]-N-tert.butyldecahydro-(4aR,8aS)-isoquinoline-3(S)-carboxamide, 4-(tert.butoxycarbonyl)-N-tert.-butyl-1- [2(R)-hydroxy-4-phenyl-3(S)-[[N-(2-quinolylcarbonyl)-L-asparaginyl]amino]butyl]-2(R or S)-piperazinecarboxamide, N-tert.-butyl-1-[2(R)-hydroxy-3(S)- [[N-(1-hydroxy-2-naphthoyl)-L-asparaginyl]amino]-4-phenylbutyl]-2(S)-piperidinecarboxamide, trans-N-tert.-butyl-decahydro-2-[2(R)-hydroxy-4-phenyl-3(S)-[[N-(2-quinolylcarbonyl)-L-asparaginyl]amino]butyl]-(4aR,8aS)-isoquinoline-3(S)-carboxamide and N-tert.-butyl-1-[2(R)-hydroxy-4-phenyl-3(S)-[[N-(2-quinolylcarbonyl)-L-cysteinyl]amino]butyl]-2-(S)-piperidinecarboxamide, together with the other compounds which are described in U.S. Pat. No. 5,157,041, the contents of which are expressly incorporated herein by reference.

Additionally, the following proteinase inhibitors are also of interest with regard to the present invention:

a) Boc-PheΨ[CH(OH)CH$_2$]Phe-Val-Phe-morpholine (also known as CGP 53437; see, for example, Alteri, El., et al., *Antimicrob. Agents Chemother.*, 37(10), 2087 (1993));

b) compounds of the following formulas:

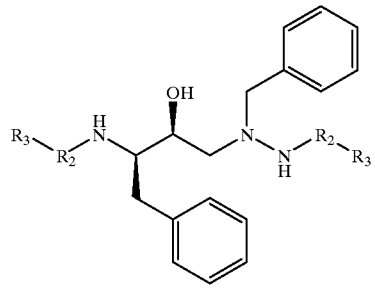

where $R_3$ is selected from Boc, acetyl, phenyl, acetyl, 3-pyridyl acetyl, 2-quinolinoyl, benzyloxycarbonyl, benzyloxycarbonyl, 4-morpholino-carbonyl, and $R_2$ is selected from L-Val or D-Val;

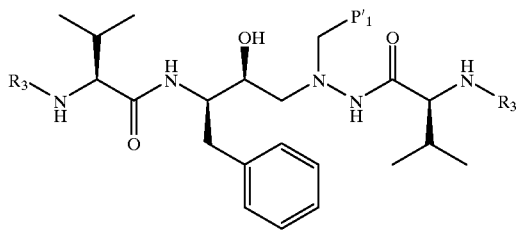

where $R_3$ is either acetyl or benzyloxycarbonyl and $P'_1$ is selected from phenyl, 4-fluorophenyl, 4-cyanophenyl, cyclohexyl, isopropyl; especially where $R_3$ is acetyl and $P'_1$ is cyclohexyl (also known as CGP 53820); see for example, Fassler, A., et al., *Bioorg. Med. Chem. Letters,* 3(12), 2837 (1993);

c) acyl derivatives of N-tert.-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide and its pharmaceutically acceptable salts wherein the hydrogen of the free hydroxy group is replaced by an acyl group. The acyl group has, for example, up to 25, preferably up to 19, carbon atoms and is especially the acyl group of a carboxylic acid bonded via its carbonyl or the acyl group of an unsubstituted or substituted amino acid, also aminocarbonyl or the radical of an N-substituted carbamic acid bonded via its aminocarbonyl group or the radical of a semi-ester of carbonic acid bonded via carbonyl.

Preferred acyl groups of a carboxylic acid are, for example, unsubstituted alkanoyl, alkenoyl or alkynoyl, or substituted alkanoyl, alkenoyl or alkynoyl, especially octanoyl, decanoyl, dodecanoyl or palmitoyl, unsubstituted or substituted lower alkanoyl, lower alkenoyl or lower alkynoyl, wherein the substituents are selected, for example, from one or more radicals, preferably from up to three radicals, especially from one radical or two radicals selected from the group consisting of hydroxy, lower alkoxy, lower alkoxy-lower alkoxy, lower alkoxy-lower alkoxy-lower alkoxy, phenoxy, naphthyloxy, phenyl-lower alkoxy, 2-halo-lower alkanoyl, such as 2-chloroacetyl, amino-, lower alkylamino- or di-lower alkylamino-lower alkoxy-2-lower alkanoyl, such as dimethylamino-lower alkoxyacetyl, amino-, lower alkylamino- or di-lower alkylamino-lower alkoxy-lower alkoxy-2-lower alkanoyl, such as dimethylamino-(2-lower alkoxyethyl)acetyl, lower alkanoyloxy, phenyl-lower alkanoyloxy, such as benzoyloxy or phenylacetoxy, halogen, such as fluorine, chlorine, bromine or iodine, especially fluorine or chlorine, carboxy, lower alkoxycarbonyl, phenyl-lower alkoxycarbonyl, such as benzyloxycarbonyl, carbamoyl, lower alkyl-carbamoyl, hydroxy-lower alkylcarbamoyl, di-lower alkylcarbamoyl, bis(hydroxy-lower alkyl)carbamoyl, carbamoyl the nitrogen atom of which is a constituent of a 5- to 7-membered heterocyclic ring that may contain a further hetero atom selected from oxygen, sulfur, nitrogen and lower alkyl-substituted, such as methyl- or ethyl-substituted, nitrogen, for example pyrrolidinocarbonyl, morpholinocarbonyl, thiomorpholino-carbonyl, piperidin-1-ylcarbonyl, piperazin-1-ylcarbonyl or 4-lower alkylpiperazin-1-ylcarbonyl, such as 4-methylpiperazin-1-ylcarbonyl; cyano, oxo, cycloalkyl, for example $C_3$–$C_8$ cycloalkyl, such as cyclopropyl, cyclobutyl, cyclopentyl or cyclohexyl, bicycloalkyl, for example $C_6$–$C_{12}$ bicycloalkyl, such as decahydronaphth-2-yl, endo- or exo-2-norbonyl, bicyclo[2.2.2]oct-2-yl or bicyclo[3.3.1]non-9-yl, tricycloalkyl, for example $C_9$–$C_{14}$ tricycloalkyl, such as 1- or 2-adamantyl, cycloalkenyl, for example $C_4$–$C_8$ cyclo-alkenyl, such as 1-cyclohexenyl or 1,4-cyclohexadienyl, bicycloalkenyl, for example 5-norbornen-2-yl or bicyclo[2.2.2]octen-2-yl, heterocyclyl, which is a saturated, partially saturated or unsaturated ring containing from 3 to 7, preferably from 5 to 7, ring atoms and up to four heteroatoms independently selected from nitrogen, sulfur and oxygen, preferably 1 or 2 of the mentioned heteroatoms, the ring being present as such or in once or twice, preferably once, benzo-, cyclopenta-, cyclohexa- or cyclohepta-fused form, heterocyclyl being unsubstituted or substituted especially by lower alkyl, lower alkanoyl, hydroxy, lower alkoxy, phenyl-lower alkoxy, such as benzyloxy, hydroxy-lower alkyl, such as hydroxymethyl, halogen, cyano and/or by trifluoromethyl, for example pyrrolyl, 2,5-dihydropyrrolyl, furanyl, thienyl, tetrahydrofuranyl, cyclohepta[b]pyrrolyl, pyrrolidinyl, imidazolyl, imidazolidinyl, pyrazolinyl, pyrazolidinyl, triazolyl, such as 1,2,3-, 1,2,4- or 1,3,4-triazolyl, tetrazolyl, such as 1- or 2-tetrazolyl, tetrahydro-oxazolyl, tetrahydro-isoxazolyl, tetrahydro-thiazolyl, tetrahydro-isothiazolyl, indolyl, isoindolyl, quinolyl, isoquinolyl, benzimidazolyl, benzofuranyl, pyridyl, pyrimidinyl, piperidinyl, piperazin-1-yl, morpholino, thiomorpholino, S,S-dioxothiomorpholino, 1,2-dihydro- or 1,2,3,4-tetrahydroquinolyl, or 1,2-dihydro- or 1,2,3,4-tetrahydro-isoquinolyl, the mentioned radicals being unsubstituted or substituted as above, especially by lower alkyl, for example as in 4-lower alkyl-piperazin-1-yl, such as 4-methyl- or 4-ethyl-piperazin-1-yl, by lower alkanoyl, for example as in 4-lower alkanoyl-piperazin-1-yl, such as 4-acetyl-piperazin-1-yl, or by hydroxy-lower alkyl, for example as in 5-hydroxy-methylfuran-2-ylcarbonyl; and aryl, preferably $C_6$–$C_{12}$ aryl, for example phenyl, naphthyl, such as 1- or 2-naphthyl, indanyl, such as 1- or 2-indanyl, indenyl, such as inden-1-yl, or fluorenyl, such as fluoren-9-yl, aryl being unsubstituted or mono- or poly-substituted, preferably mono-substituted, for example, by lower alkyl, for example methyl, halo-lower alkyl, such as chloro- or bromo-methyl, halogen, for example fluorine or chlorine, hydroxy, lower alkoxy, such as methoxy, lower alkanoyloxy, carboxy, lower alkoxycarbonyl, phenyl-lower alkoxycarbonyl, carbamoyl, mono- or di-lower alkylcarbamoyl, mono- or di-hydroxy-lower alkylcarbamoyl, halo-lower alkyl, such as trifluoromethyl, heterocyclyl-lower alkyl wherein heterocyclyl is as defined above, especially heterocyclylmethyl wherein heterocyclyl is bonded via a ring nitrogen atom, for example piperidinomethyl, piperazin-1-ylmethyl, 4-lower alkyl-piperazin-1-yl methyl, such as 4-methyl- or 4-ethyl-piperazin-1-ylmethyl, 4-lower alkanoyl-piperazin-1-ylmethyl, such as 4-acetyl-piperazin-1-ylmethyl, morpholinomethyl or thiomorpholinomethyl, cyano and/or by nitro, and especially phenyl substituted in the p-position by one of the mentioned radicals; for example lower alkanoyl, such as formyl, acetyl, propionyl, butyryl, methylpropionyl, pivaloyl, n-pentanoyl, hexanoyl or heptanoyl, such as n-heptanoyl, hydroxy-lower alkanoyl, for example β-hydroxypropionyl, lower alkoxy-lower alkanoyl, for example lower alkoxyacetyl or lower alkoxypropionyl, such as methoxyacetyl, 3-methoxypropionyl or n-butoxyacetyl, lower alkoxy-lower alkoxy-lower alkanoyl, such as 2-(2-methoxy-ethoxy)acetyl, lower alkoxy-lower alkoxy-lower alkoxy-lower alkanoyl, such as 2-(2-(2-methoxyethoxy) ethoxy)acetyl, phenoxy-lower alkanoyl, for example phenoxy-acetyl, naphthyloxy-lower alkanoyl, for example a- or b-naphthyloxyacetyl, phenyl-lower alkoxy-lower alkanoyl, such as benzyloxyacetyl, 2-halo-lower alkanoyl, such as 2-chloro-acetyl, amino-, lower alkylamino- or di-lower alkylamino-lower alkoxy-2-lower alkanoyl, such as dimethylamino-lower alkoxyacetyl, amino-, lower alkylamino- or di-lower alkyl-amino-lower alkoxy-lower alkoxy-2-lower alkanoyl, such as dimethylamino-(2-lower alkoxyethoxy)acetyl, lower alkanoyloxy-lower alkanoyl, for example lower alkanoyloxy-acetyl or lower alkanoyloxypropionyl, such as acetoxyacetyl or β-acetoxypropionyl, halo-lower alkanoyl, for example α-haloacetyl, such as α-chloro-, α-bromo-, α-iodo-, α,α,α-tri-fluoro- or α,α,α-trichoro-acetyl, or halopropionyl, such as β-chloro or β-bromo-propionyl, carboxy-lower alkanoyl, for example carboxyacetyl or 3-carboxypropionyl, lower alkoxycarbonyl-lower alkanoyl, for example lower alkoxy-carbonylacetyl or lower alkoxycarbonylpropionyl, such as methoxycarbonylacetyl, β-methoxycarbonylpropionyl, ethoxycarbonylacetyl, β-ethoxycarbonylpropionyl, tert-butoxycarbonylacetyl or β-tert-butoxycarbonylpropionyl, carbamoyl-lower alkanoyl, for example carbamoylacetyl or β-carbamoylpropionyl, lower alkylcarbamoyl-lower alkanoyl, for example methyl-carbamoylacetyl or b-(N-lower alkyl)carbamoylpropionyl, such as β-(N-methyl)-, β-(N-ethyl)-, β-(N-(n-propyl))-carbamoyl- or β-(N-(n-hexyl))-carbamoyl-propionyl, di-lower alkylcarbamoyl-lower alkanoyl, for example dimethylcarbamoylacetyl, β-(N,N-(di-lower alkyl)carbamoyl)propionyl, such as β-(N, N-dimethyl)-, β-(N,N-di-ethyl)-, β-(N,N-di(n-propyl)-carbamoyl)- or β-(N,N-di-(n-hexyl))-carbamoyl-propionyl, β-pyrrolidinocarbonylpropionyl, β-morpholinocarbonylpropionyl, β-thiomorpholino-carbonylpropionyl, β-piperidin-1-ylcarbonylpropionyl, β-piperazin-1-ylcarbonylpropionyl or β-(4-lower alkyl-piperazin-1-ylcarbonyl)-propionyl, such as β-(4-methylpiperazin-1-yl-carbonyl)propionyl, oxo-lower alkanoyl, for example acetoacetyl or propionylacetyl, hydroxy-carboxy-lower alkanoyl, for example a-hydroxy-a-carboxy-acetyl or a-hydroxy-β-carboxypropionyl, hydroxy-lower alkoxycarbonyl-lower alkanoyl, for example α-hydroxy-α-ethoxy- or -methoxy-carbonylacetyl or α-hydroxy-β-ethoxy- or -methoxy-carbonyl-propionyl, α-acetoxy-α-methoxycarbonyl-acetyl, dihydroxy-carboxy-lower alkanoyl, for example α,β-dihydroxy-β-carboxy-propionyl, dihydroxy-lower alkoxycarbonyl-lower alkanoyl, for example, α,β-dihydroxy-β-ethoxy- or -methoxy-carbonyl-propionyl, α,β-diacetoxy-β-methoxycarbonyl-propionyl, α-naphthyloxy-carboxy-lower alkanoyl, for example 2-α-naphthyloxy-4-carboxy-butyryl, α-naphthyl-oxy-lower alkoxycarbonyl, lower alkanoyl, for example α-naphthyloxy-ethoxycarbonyl-acetyl, 2-α-naphthyloxy-ethoxycarbonyl-propionyl or 2-α-naphthyloxy-4-tertbutoxy-carbonylbutyryl, α-naphthyloxy-benzyloxycarbonyl-lower alkanoyl, for example 2-α-naphthyoxy-3-benzyloxycarbonyl-propionyl, α-naphthyloxy-carbamoyl-lower alkanoyl, for example 2-α-naphthyloxy-4-carbamoyl-butyryl, α-naphthyloxy-cyano-lower alkanoyl, for example α-naphthyloxy-cyano-acetyl or 2-α-naphthyloxy-4-cyanobutyryl, α-naphthyloxy-oxo-lower alkanoyl, for example 2-α-naphthyloxy-4-oxo-pentanoyl, heterocyclyl-lower alkanoyl, for example unsubstituted or substituted pyrrolylcarbonyl, for example 2- or 3-pyrrolylcarbonyl, furylcarbonyl, for example 2-furylcarbonyl, 5-hydroxymethyl-furan-2-ylcarbonyl, thienylcarbonyl, for example 2-thienylcarbonyl, pyridyl-lower alkanoyl, such as pyridylcarbonyl, for example 2-, 3- or 4-pyridylcarbonyl, pyridylacetyl, for example 2-pyridylacetyl, or pyridylpropionyl, for example 3-(2-pyridyl)-propionyl, quinolylcarbonyl, such as quinolin-2-ylcarbonyl, isoquinolinylcarbonyl, such as isoquinolin-3-ylcarbonyl, unsubstituted or substituted indolylcarbonyl, for example 2-, 3- or 5-indolylcarbonyl, 1-methyl-, 5-methyl-, 5-methoxy-, 5-benzyloxy-, 5-chloro- or 4,5-dimethyl-indolyl-2-carbonyl, cyclohepta[b]pyrrolyl-5-carbonyl, pyrrolidin-(2- or 3-)yl-carbonyl(pyrrolidinyl-2-carbonyl(= prolyl) preferably being in the D- or L-form), hydroxypyrrolidinylcarbonyl, for example 3- or 4-hydroxypyrrolidinyl-2-carbonyl, oxo-pyrrolidinylcarbonyl, for example 5-oxopyrrolidinyl-2-carbonyl, piperidinylcarbonyl, for example 2-, 3- or 4-piperidinylcarbonyl, 1,2,3,4-tetrahydroquinolylcarbonyl, for example 1,2,3,4-tetrahydroquinolyl-2-, -3- or -4-carbonyl, or 1,2,3,4-tetrahydroisoquinolylcarbonyl, for example 1,2,3,4-tetrahydroisoquinolyl-1-, -3- or -4-carbonyl, imidazoyl-lower alkanoyl, such as imidazolylcarbonyl, for example imidazol-1-ylcarbonyl or imidazol-4-ylcarbonyl, imidazolylacetyl, for example 4-imidazolylacetyl, or imidazolylpropionyl, for example 3-(4-imidazolyl)propionyl, morpholinocarbonyl, thiomorpholinocarbonyl, morpholinoacetyl, thiomorpholinoacetyl, 4-lower alkyl-1-piperazinoacetyl, such as 4-methyl-piperazinoacetyl, indolylacetyl or benzofuranylacetyl, lower alkenoyl, for example acryloyl, vinylacetyl, crotonoyl or 3- or 4-pentenoyl, lower alkynoyl, for example propioloyl or 2- or 3-butynoyl, cycloalkylcarbonyl, for example cyclopropyl-, cyclobutyl-, cyclopentyl- or cyclohexyl-carbonyl, bicycloalkylcarbonyl, for example decahydro-naphthyl-2-carbonyl, endo- or exo-norbornyl-2-carbonyl, bicyclo[2.2.2]oct-2-ylcarbonyl or bicyclo[3.3.f]non-9-ylcarbonyl, tricycloalkylcarbonyl, for example 1- or 2-adamantyl-carbonyl, cycloalkenylcarbonyl, for example 1-cyclohexenylcarbonyl or 1,4-cyclohexadienylcarbonyl, bicycloalkenylcarbonyl, for example 5-norbornen-2-ylcarbonyl or bicyclo[2.2.2]octen-2-ylcarbonyl, cyclopropylacetyl, cyclopentylacetyl, cyclohexylacetyl or 3-cyclohexylpropionyl, cycloalkyl-lower alkenoyl, for example cyclohexylacryloyl, cycloalkenyl-lower alkanoyl, for example 1-cyclohexenylacetyl or 1,4-cyclohexadienyl-acetyl, phenyl-lower alkanoyl, for example benzoyl, phenylacetyl or 3-phenylpropionyl, that is unsubstituted or mono- or poly-substituted in the phenyl radical by lower alkyl, for example methyl, halo-lower alkyl, such as chloro- or bromo-methyl, halogen, for example fluorine or chlorine, hydroxy, lower alkoxy, for example methoxy, piperidinomethyl, piperazin-1-ylmethyl, 4-lower alkyl-piperazin-1-ylmethyl, such as 4-methyl- or 4-ethyl-piperazin-1-ylmethyl, 4-lower alkanoyl-piperazin-1-ylmethyl, such as 4-acetyl-piperazin-1-ylmethyl, morpholinomethyl, thiomorpholinomethyl, cyano and/or by nitro, or α-naphthyl- or β-naphthyl-lower alkanoyl wherein naphthyl is unsubstituted or mono- or poly-substituted by lower alkyl, for example methyl, phenyl, halogen, for example chlorine, hydroxy, lower alkoxy, for example methoxy, and/or by nitro, and lower alkanoyl in phenyl-, α-naphthyl-or β-naphthyl-lower alkanoyl may be unsubstituted or substituted, for example, by hydroxy, lower alkoxy, lower alkanoyloxy, carboxy, lower alkoxycarbonyl, phenyl-lower alkoxycarbonyl, such as benzyloxycarbonyl, carbamoyl, lower alkylcarbamoyl, di-lower alkoxycarbamoyl, cyano and/or by oxo and may be branched, for example 4-chloromethyl-, 4-bromomethyl-, 4-fluoro-, 4-chloro-, 4-methoxy-, 4-morpholinomethyl-, 4-thiomorpholinomethyl-, 4-cyano- or 4-nitro-benzoyl, α-naphthylacetyl, β-naphthylacetyl, lower alkylphenylacetyl, such as 4-methyl-phenylacetyl, lower alkoxyphenylacetyl, such as 4-methoxyphenylacetyl, 2-lower alkoxy-2-phenylacetyl, such as (R)- or (S)-2-methoxy-2-phenylacetyl, 3-(p-hydroxy-phenyl)-propionyl, diphenylacetyl, di(4-methoxyphenyl)acetyl, triphenylacetyl, 3-α- or 3-β-naphthylpropionyl, 3-phenyl- or 3-α-naphthyl-2-hydroxy-propionyl, 3-phenyl- or 3-α-naphthyl-2-lower alkoxy-propionyl, such as 3-phenyl or 3-α-naphthyl-2-neopentyloxy-propionyl, 3-phenyl-2-pivaloyloxy- or -2-acetoxy-propionyl, 3-α-naphthyl-2-pivaloyloxy- or -2-acetoxy-propionyl, 3-phenyl- or 3-α-naphthyl-2-carboxymethylpropionyl, 3-phenyl- or 3-α-naphthyl-2-lower alkoxycarbonyl-propionyl, such as 3-α-naphthyl-2-ethoxycarbonyl-propionyl, 3-phenyl- or 3-α-naphthyl-2-benzyloxycarbonylmethyl-propionyl, 3-phenyl- or 3-α-naphthyl-2-carbamoyl-propionyl, 3-phenyl- or 3-α-naphthyl-2-tert-butylcarbamoyl-propionyl, 3-phenyl- or 3-α-naphthyl-2-cyano-propionyl, 3-phenyl- or 3-αnaphthyl-2-cyanomethyl-propionyl, 3-phenyl- or 3-α-naphthyl-2-acetenyl-propionyl, 2-benzyl- or 2-α-naphthylmethyl-4-cyano-butyryl, 4-phenyl- or 4-α-naphthyl-3-carboxy-butyryl, 4-phenyl- or 4-α-naphthyl-3-benzlyoxycarbonyl-butyryl, 2-benzyl- or 2-α-naphthylmethyl-4-oxo-pentanoyl, phenyl-lower alkenoyl, for example β-phenyl-acryloyl or β-phenylvinylacetyl, naphthylcarbonyl, for example α- or β-naphthylcarbonyl, indenylcarbonyl, for example 1-, 2- or 3-indenylcarbonyl, or indanylcarbonyl, for example 1- or 2-indanylcarbonyl.

Preferred acyl groups of a semiester of carbonic acid are, for example, unsubstituted or substituted alkoxycarbonyl, especially lower alkoxycarbonyl, for example methoxy-, ethoxy- or tert-lower alkoxy-carbonyl, such as tert-butoxycarbonyl, 2-halo-lower alkoxy-carbonyl, for example 2-chloro-, 2-bromo-, 2-iodo- or 2,2,2-trichloro-ethoxycarbonyl; aryl-lower alkoxycarbonyl, for example arylmethoxycarbonyl, wherein aryl preferably has from 6 to 14 carbon atoms, is unsubstituted or mono- or poly-substituted, preferably mono-substituted, for example, by lower alkyl, for example methyl, halo-lower alkyl, such as chloro- or bromo-methyl, halogen, for example fluorine or chlorine, hydroxy, lower alkoxy, such as methoxy, lower alkanoyloxy, carboxy, lower alkoxycarbonyl, phenyl-lower alkoxycarbonyl, carbamoyl, mono- or di-lower alkylcarbamoyl, mono- or di-hydroxy-lower alkylcarbamoyl, halo-lower alkyl, such as trifluoromethyl, heterocyclyl-lower alkyl wherein heterocyclyl is as defined above as a substituent of lower alkanoyl, especially heterocyclylmethyl wherein heterocyclyl is bonded via a ring nitrogen atom, for example piperidinomethyl, piperazin-1-ylmethyl, 4-lower alkyl-piperazin-1-ylmethyl, such as 4-methyl- or 4-ethyl-piperazin-1-ylmethyl, 4-lower alkanoyl-piperazin-1-ylmethyl, such as 4-acetyl-piperazin-1-ylmethyl, morpholinomethyl or thiomorpholinomethyl, cyano and/or by nitro, and is especially phenyl, 1- or 2-naphthyl, fluorenyl or phenyl mono- or poly-substituted by lower alkyl, for example methyl or tert-butyl, lower alkoxy, for example methoxy, ethoxy or tert-butoxy, hydroxy, halogen, for example fluorine, chlorine or bromine, and/or by nitro, for example phenyl-lower alkoxycarbonyl, such as benzyloxycarbonyl, 4-methoxybenzyloxycarbonyl, 4-nitrobenzyloxycarbonyl, diphenyl-lower alkoxycarbonyl, such as diphenylmethoxycarbonyl, di(4-methoxyphenyl) methoxycarbonyl, trityloxycarbonyl or fluorenyl-lower alkoxycarbonyl, such as 9-fluorenyl-methoxycarbonyl; or also heterocyclyl-lower alkoxycarbonyl wherein heterocyclyl is as defined above as a substitutent of alkanoyl, for example furan-2-ylmethoxycarbonyl or pyridin-2-, -3- or -4-ylmethoxycarbonyl.

A preferred acyl group of an N-substituted carbamic acid is an aminocarbonyl radical wherein the amino group carries one or two substituents selected independently of one another from unsubstituted or substituted lower alkyl, the substituents of which are selected from those mentioned above for substituted lower alkanoyl and are present in the number defined therein, preferably substituents selected from hydroxy, lower alkoxy, phenoxy, naphthyloxy, lower alkanoyloxy, phenyl-lower alkanoyloxy, such as benzoyloxy or phenylacetoxy, halogen, such as fluorine, chlorine, bromine or iodine, especially fluorine or chlorine, carboxy, lower alkoxycarbonyl, phenyl-lower alkoxycarbonyl, such as benzyloxycarbonyl, carbamoyl, lower alkylcarbamoyl, hydroxy-lower alkylcarbamoyl, di-lower alkylcarbamoyl, bis(hydroxy-lower alkyl)carbamoyl, cyano, oxo and $C_6$–$C_{12}$ aryl, for example phenyl, naphthyl, such as 1- or 2-naphthyl, indanyl, such as 1- or 2-indanyl, indenyl, such as inden-1-yl, or fluorenyl, such as fluoren-9-yl, aryl being unsubstituted or mono- or poly-substituted, preferably mono-substituted, for example, by lower alkyl, for example methyl, halo-lower alkyl, such as chloro- or bromo-methyl, halogen, for example, fluorine or chlorine, hydroxy, lower alkoxy, such as methoxy, lower alkanoyloxy, carboxy, lower alkoxycarbonyl, phenyl-lower alkoxycarbonyl, carbamoyl, mono- or di-lower alkylcarbamoyl, mono- or di-hydroxy-lower alkylcarbamoyl, halo-lower alkyl, such as trifluoromethyl, cyano and/or by nitro, especially phenyl substituted in the p-position by one of the mentioned radicals; especially unsubstituted lower alkyl, such as methyl or ethyl; and aryl which preferably has from 6 to 14 carbon atoms and is unsubstituted or mono- or poly-substituted, preferably mono-substituted, for example, by lower alkyl, for example methyl, halo-lower alkyl, such as chloro- or bromo-methyl, halogen, for example fluorine or chlorine, hydroxy, lower alkoxy, such as methoxy, lower alkanoyloxy, carboxy, lower alkoxycarbonyl, phenyl-lower alkoxycarbonyl, carbamoyl, mono- or di-lower alkylcarbamoyl, mono- or di-hydroxy-lower alkylcarbamoyl, halo-lower alkyl, such as tri-fluoromethyl, heterocyclyl-lower alkyl wherein heterocyclyl is as defined above as a substituent of lower alkanoyl, especially heterocyclylmethyl wherein heterocyclyl is bonded via a ring nitrogen atom, for example piperidinomethyl, piperazin-1-ylmethyl, 4-lower alkyl-piperazin-1-ylmethyl, such as 4-methyl- or 4-ethyl-piperazin-1-ylmethyl, 4-lower alkanoyl-piperazin-1-ylmethyl, such as 4-acetyl-piperazin-1-ylmethyl, morpholinomethyl or thiomorpholinomethyl, cyano and/or by nitro, preferably correspondingly substituted phenyl or 1- or 2-naphthyl, the radical of an N-substituted carbamic acid carrying not more than one of the mentioned aryl radicals at the nitrogen atom; an acyl group of an N-substituted carbamic acid is especially mono- or di-lower alkylaminocarbonyl, such as N-methyl-, N-ethyl-, N,N-dimethyl- or N,N-diethyl-aminocarbonyl, or phenyl-lower alkylaminocarbonyl wherein phenyl is unsubstituted or substituted by the radicals mentioned in the definition of aryl, for example by lower alkyl, for example methyl, halo-lower alkyl, such as chloro- or bromo-methyl or trifluoromethyl, halogen, for example fluorine or chlorine, hydroxy, lower alkoxy, such as methoxy, carboxy and/or by cyano, preferably by up to three of those substituents selected independently of one another, especially by one of those substituents, for example in the p-position, such as in N-benzyl-, N-(4-fluorobenzyl)-, N-(4-chlorobenzyl)-, N-(4-trifluoromethyl-benzyl)- or N-(4-cyanobenzyl)-aminocarbonyl; especially preferred is aminocarbonyl substituted by only one radical at the nitrogen atom, for example N-lower alkylaminocarbonyl, such as N-methyl- or N-ethyl-aminocarbonyl, or phenyl-lower alkylaminocarbonyl wherein phenyl is unsubstituted or substituted by the radicals mentioned in the definition of aryl, for example by lower alkyl, such as methyl, halo-lower alkyl, such as chloro- or bromo-methyl or trifluoromethyl, halogen, such as fluorine or chlorine, hydroxy, lower alkoxy, such as methoxy, carboxy and/or by cyano, preferably by up to three of those substituents selected independently by one another, especially by one of those substituents, for example in the p-position, such as in N-benzyl-, N-(4-fluorobenzyl)-, N-(4-chlorobenzyl)-, N-(4-trifluoromethylbenzyl)- or N-(4-cyanobenzyl)-aminocarbonyl.

Preferred acyl groups of an unsubstituted or substituted amino acid are formed by the amino acid residues of an α-, β-, γ-, or δ-amino acid that is bonded via its carbonyl group, especially of a natural α-amino acid having the L-configuration, such as those normally occurring in proteins, or an epimer of such an amino acid, that is to say having the unnatural D-configuration, or a D,L-isomeric mixture thereof, a homologue of such an amino acid, for example wherein the amino acid side chain has been lengthened or shortened by one or two methylene groups, wherein the amino group is in the β-, γ-, or δ-position and/or wherein a methyl group has been replaced by hydrogen, a substituted aromatic amino acid wherein the aromatic radical has from 6 to 14 carbon atoms, for example a substituted phenylalanine or phenylglycine wherein the phenyl may be mono- or poly-substituted by lower alkyl, for example methyl, hydroxy, lower alkoxy, for example methoxy, lower alkanoyloxy, for example acetoxy, amino, lower alkylamino, for example methylamino, di-lower alkylamino, for example dimethylamino, lower alkanoylamino, for example acetylamino or pivaloylamino, lower alkoxycarbonylamino, for example tert-butoxy-carbonylamino, arylmethoxycarbonylamino wherein aryl preferably has from 6 to 14 carbon atoms, for example benzyloxycarbonylamino or 9-fluorenylmethoxycarbonyl-amino, halogen, for example fluorine, chlorine, bromine or iodine, carboxy and/or by nitro, a benzo-fused phenylalanine or phenylglycine, such as α-naphthylalanine, or a hydrogenated phenylalanine or phenylglycine, such a cyclohexylalanine or cyclohexylglycine.

Those amino acid radicals may be substituted at free amino or hydroxy functions, preferably at a free amino function, by one of the radicals mentioned above under acyl as the acyl group of a carboxylic acid or a semiester of carbonic acid, by unsubstituted or substituted alkyl, especially lower alkyl, such as methyl, ethyl, isopropyl, n-propyl or n-butyl, wherein the substituents are selected, for example, from one or more radicals, preferably from up to three radicals, especially from one radical selected from the group consisting of hydroxy, lower alkoxy, phenoxy, naphthyloxy, lower alkanoyloxy, halogen, such as fluorine, chlorine, bromine or iodine, especially fluorine or chlorine, carboxy, lower alkoxycarbonyl, phenyl-lower alkoxycarbonyl, such as benzyloxycarbonyl, carbamoyl, lower alkylcarbamoyl, hydroxy-lower alkylcarbamoyl, di-lower alkylcarbamoyl, bis(hydroxylower alkyl) carbamoyl, cyano, oxo, cycloalkyl, for example $C_3$–$C_8$ cycloalkyl, such as cyclopropyl, cyclobutyl, cyclopentyl or cyclohexyl, bicycloalkyl, for example $C_6$–$C_{12}$ bicycloalkyl, such as decahydronaphth-2-yl, endo- or exo-2-norbornyl-bicyclo[2.2.2]oct-2-yl or bicyclo[3.3.1]non-9-yl, tricycloalkyl, for example $C_9$–$C_{14}$ tricycloalkyl, such as 1- or 2-adamantyl, cycloalkenyl, for example $C_4$–$C_8$ cycloalkenyl, such as 1-cyclohexenyl or 1,4-cyclohexadienyl, bicycloalkenyl, for example 5-norbornen-2-yl or bicyclo[2.2.2]octen-2-yl, heterocyclyl, which is a saturated, partial saturated or unsaturated ring containing from 3 to 7, preferably from 5 to 7, ring atoms and up to four heteroatoms independently selected from nitrogen, sulfur and oxygen, preferably 1 or 2 of the mentioned heteroatoms, the ring being present as such or in once or twice, preferably once, benzo-, cyclopenta-, cyclohexa-or cyclohepta-fused form, heterocyclyl being unsubstituted or substituted especially by lower alkyl, lower alkanoyl, hydroxy, lower alkoxy, phenyl-lower alkoxy, such as benzyloxy, hydroxy-lower alkyl, such as hydroxymethyl, halogen, cyano and/or by trifluoromethyl, for example pyrrol-2,5-dihydropyrrolyl, furanyl, thienyl, tetrahydrofuranyl, cyclohepta[b]pyrrolyl, pyrrolidinyl, imidazolyl, imidazolidinyl, pyrazolinyl, pyrazolidinyl, triazolyl, such as 1,2,3-, 1,2,4- or 1,3,4-triazolyl, tetrazolyl, such as 1- or 2-tetrazolyl, tetrahydro-oxazolyl, tetrahydro-isoxazolyl, tetrahydro-thiazolyl, tetrahydro-isothiazolyl, indolyl, isoindolyl, quinolyl, isoquinolyl, benzimidazolyl, benzofuranyl, pyridyl, pyrimidinyl, piperidinyl, piperazin-1-yl, morpholino, thiomorpholino, S, S-dioxothiomorpholino, 1,2-dihydro- or 1,2,3,4-tetrahydro-quinolyl, or 1,2-dihydro- or 1,2,3,4-tetrahydro-isoquinolyl, the mentioned radicals being unsubstituted or substituted as mentioned above, especially by lower alkyl, for example as in 4-lower alkyl-piperazin-1-yl, such as 4-methyl- or 4-ethyl-piperazin-1-yl, or by lower alkanoyl, for example as in 4-lower alkanoyl-piperazin-1-yl, such as 4-acetyl-piperazin-1-yl, and aryl, preferably $C_6$–$C_{12}$ aryl, for example phenyl, naphthyl, such as 1- or 2-naphthyl, indanyl, such as 1- or 2-indanyl, indenyl, such as inden-1-yl, or fluoren-9-yl, the mentioned aryl radicals being unsubstituted or mono- or poly-substituted, preferably mono-substituted, for example, by lower alkyl, for example methyl, halo-lower alkyl, such as chloro- or bromo-methyl, halogen, for example fluorine or chlorine, hydroxy, lower alkoxy, such as methoxy, lower alkanoyloxy, carboxy, lower alkoxycarbonyl, phenyl-lower alkoxycarbonyl, carbamoyl, mono- or di-lower alkoxycarbamoyl, mono- or di-hydroxy-lower alkylcarbamoyl, halo-lower alkyl, such as trifluoromethyl, heterocyclyl-lower alkyl wherein heterocyclyl is as defined above, especially heterocyclylmethyl wherein heterocyclyl is bonded via a ring nitrogen atom, for example piperidinomethyl, piperazin-1-ylmethyl, 4-lower alkyl-piperazin-1-ylmethyl, such as 4-methyl- or 4-ethyl-piperazin-1-ylmethyl, 4-lower alkanoyl-piperazin-1-ylmethyl, such as 4-acetyl-piperazin-1-ylmethyl, morpholinomethyl, thiomorpholinomethyl, cyano and/or by nitro, especially phenyl substituted in the p-position by one of the mentioned radicals; especially by the correspondingly substituted lower alkyl radical, especially correspondingly substituted methyl, preferably benzyl, diphenylmethyl, trityl, 2-, 3- or 4-pyridylmethyl, or may be substituted by one of the radicals mentioned as protecting groups in the section relating to processes, or may be derivatised at carboxy groups.

Especially preferred is the residue, bonded via its a-carbonyl group, of an amino acid selected from glycine (H—Gly—OH), alanine (H—Ala—OH), 2-aminobutyric acid, 3-aminobutyric acid, 4-aminobutyric acid, 3-aminopentanoic acid, 4-aminopentanoic acid, 5-aminopentanoic acid, 3-aminohexanoic acid, 4-aminohexanoic acid or 5-aminohexanoic acid, valine (H—Val—OH), norvaline (α-aminovaleric acid), leucine (H—Leu—OH), isoleucine (H—Ile—OH), norleucine (α-aminohexanoic acid, H—Nle—OH), serine (H—Ser—OH), homoserine (α-amino-γ-hydroxybutyric acid), threonine (H—Thr—OH), methionine (H—Met—OH), cystein (H—Cys—OH), phenylalanine (H—Phe—OH), tyrosine (H—Tyr—OH), 4-aminophenylalanine, 4-chloro-phenylalanine, 4-carboxylphenylalanine, β-phenylserine (β-hydroxyphenylalanine), phenylglycine, α-naphthylalanine (H—Nal—OH), cyclohexylalanine (H—Cha—OH), cyclohexylglycine, tryptophan (H—Trp—OH), aspartic acid (H—Asp—OH), asparagine (H—Asn—OH), aminomalonic acid, aminomalonic acid monoamide, glutamic acid (H—Glu—OH), glutamine (H—Gln—OH), histidine (H—His—OH), arginine (H—Arg—OH), lysine (H—Lys—OH), d-hydroxylysine, ornithine (α,δ-diaminovaleric acid), 3-aminopropanoic acid, α,γ-diaminobutyric acid and α,β-diaminopropionic acid, especially the residue of an aliphatic amino acid selected from alanine, valine, norvaline, leucine, 3-aminopropionic acid, 2-aminobutyric acid, 3-aminobutyric acid, 4-aminobutyric acid, 3-aminopentanoic acid, 4-aminopentanoic acid, 5-aminopentanoic acid, 3-aminohexanoic acid, 4-aminohexanoic acid or 5-aminohexanoic acid and isoleucine or an amino acid selected from glycine, asparagine, glutamine, methionine, lysine and phenylalanine, it being possible for each of the mentioned amino acids to be in the D-, L- or (D,L)-form, preferably in the L-form (except in cases where there is no asymmetric carbon atoms, for example in the case of glycine), an α-amino group, if present, is unsubstituted or is mono- or di-N-alkylated, for example by lower alkyl, such as methyl, n-propyl or n-butyl, by amino-lower alkyl, such as 3-aminopropyl, by phenyl- or naphthyl-amino-lower alkyl, such as 3-phenylamino-propyl, by phenyl-lower alkyl, such as benzyl, by diphenylmethyl, by trityl and/or by heterocyclyl-lower alkyl wherein heterocyclyl is as defined above for an acyl group of a carboxylic acid, especially by heterocyclylmethyl, for example furanyl-lower alkyl, such as 2-furylmethyl, thienyl-lower alkyl, such as 2-thienylmethyl, imidazolyl-lower alkyl, such as imidazol-4-ylmethyl, or 2-, 3- or 4-pyridyl-lower alkyl, such as 2-, 3- or 4-pyridyl-methyl, and/or is N-acylated, for example, by the acyl groups of a carboxylic acid mentioned above, especially by unsubstituted or substituted lower alkanoyl, as defined above, especially by acetyl, propionyl, pivaloyl, heterocyclyl-lower alkanoyl, as defined above, for example furan-2-ylcarbonyl, 5-hydroxy-methyl-furan-2-ylcarbonyl, 2-, 3- or 4-pyridylcarbonyl, morpholinocarbonyl, thiomorpholinocarbonyl, indolylacetyl or benzofuranylacetyl, aryl-lower alkanoyl, such as benzoyl or phenylacetyl, or the acyl groups of a semiester of carbonic acid mentioned above, especially lower alkoxycarbonyl, such as tert-butoxycarbonyl, or aryl-lower alkoxycarbonyl, such as benzyloxycarbonyl, a carboxy group of the side chain is present in free form or in esterified or amidated form, for example in the form of a lower alkyl ester group, such a methoxycarbonyl or tert-butoxycarbonyl, an aryl ester group or an aryl-lower alkyl ester group, wherein aryl is phenyl, 4-nitrophenyl, naphthyl, fluorenyl or biphenylyl, for example in the form of a 4-nitrophenoxycarbonyl, benzyloxycarbonyl or 9-fluorenylmethoxycarbonyl group, or in the form of a carbamoyl, a lower alkylcarbamoyl, such as methylcarbamoyl, a di-lower alkylcarbamoyl, such as dimethylcarbamoyl, a mono- or di(hydroxy-lower alkyl)-carbamoyl, such as hydroxymethylcarbamoyl or di(hydroxymethyl)carbamoyl, or a mono- or di-(carboxy-lower alkyl)carbamoyl group, such as a carboxymethylcarbamoyl or di(carboxymethyl)carbamoyl group, an amino group of the side chain that is not in the a-position is present in free form or in alkylated form, for example in the form of mono- or di-lower alkylamino, such as n-butyl-amino or dimethylamino, or in acylated form, for example in the form of lower alkanoyl-amino, such as acetylamino or pivaloylamino, amino-lower alkanoylamino, such as 3-amino-3,3-dimethylpropionylamino, aryl-lower alkanoylamino wherein aryl has from 6 to 14 carbon atoms, for example phenyl, naphthyl or fluorenyl, and is unsubstituted or substituted by lower alkyl, hydroxy, lower alkoxy, carboxy, carbamoyl or by sulfamoyl, such as 4-hydroxyphenylbutyryl, lower alkoxycarbonylamino, such as tert-butoxy-carbonylamino, arylmethoxycarbonylamino wherein aryl has from 6 to 14 carbon atoms, such as benzyloxycarbonylamino or 9-fluorenylmethoxycarbonylamino, piperidyl-1-carbonyl, morpholinocarbonyl, thiomorpholino-carbonyl or S,S-dioxothiomorphoino-carbonyl, and/or a hydroxy group of the side chain is present in free form or in etherified or esterified form, for example in the form of a lower alkoxy, such as methoxy or tert-butoxy, aryl-lower alkoxy, especially phenyl-lower alkoxy, such as benzyloxy, lower alkanoyloxy, such as acetoxy, or lower alkoxycarbonyloxy group, for example a tert-butoxycarbonyloxy group.

Preference is given especially to acyl groups of an unsubstituted or substituted amino acid selected from alanyl, N-lower alkylalanyl, such as N-methylalanyl, phenylalanyl, N-(benzyloxycarbonyl)-phenylalanyl, N-(9-fluorenylmethoxycarbonyl)-phenylalanyl, aminoacetyl (glycyl), N-lower alkylaminoacetyl, N,N-di-lower alkylaminoacetyl, N-lower alkyl-N-phenyl-lower alkylaminoacetyl, N-lower alkyl-N-imidazolyl-lower alkylamino-acetyl, N-lower alkyl-N-pyridyl-lower alkylaminoacetyl, N-lower alkyl-N-lower alkoxy-carbonylaminoacetyl, N-phenyl-lower alkoxycarbonyl-N-lower alkylaminoacetyl, N-morpholino- or N-thiomorpholino-lower alkylaminoactyl, for example N-methyl-aminoacetyl, N,N-dimethylaminoacetyl, N-methyl-N-(n-butyl)aminoacetyl, N-methyl-N-benzylaminoacetyl, N-methyl-N-[(2-, 3- or 4-)pyridylmethyl]-aminoacetyl, such as N-methyl-N-(2- or 3-)pyridylmethylaminoacetyl, N-(imidazol-4-ylmethyl)-N-methyl-aminoacetyl, N-methyl-N-tert-butoxycarbonylaminoacetyl, N-benzyloxycarbonyl-N-lower alkylaminoacetyl, N-morpholinocarbonylaminoacetyl, 3-aminopropionyl, 2-aminobutyryl, 3-aminobutyryl, 4-aminobutyryl, 4-(N,N-demethylamino)butyryl, 3-aminopentanoyl, 4-aminopentanoyl, 5-aminopentanoyl, 3-aminohexanoyl, 4-aminohexanoyl or 5-aminohexanoyl, valyl, N-phenylacetyl-valyl, N-acetyl-valyl, N-(3-phenylpropionyl)-valyl, N(2-, 3- or 4-pyridylcarbonyl)-valyl, N-methoxycarbonyl-valyl, N-isobutoxycarbonyl-valyl, N-tert-butoyxcrabonyl-valyl, N-benzloyxcarbonyl-valyl, N-(morpholinocarbonyl)-valyl, norvalyl, leucyl, N-acetyl-leucyl, N-(2-, 3- or 4-pyridylcarbonyl)-leucyl, N-(benzyloxycarbonyl)-leucyl, isoleucyl, N-acetyl-isoleucyl, N-propionyl-isoleucyl, N-(benzyloxy-carbonyl)-isoleucyl, N-(tert-butoxycarbonyl)-isoleucyl, methionyl, lysyl, glutamyl, γ-(N-benzlyoxycarbonyl)-glutamyl, asparagyl and β-(N-benzyloxy-carbonyl)asparagyl, the amino acid residues preferably being in the (L)- or the (D)- or (D,L)-form (except in case where there is no asymmetric carbon atom, for example in the case of Gly).

In these compounds, if hydroxy or amino groups having a free hydrogen atom are located at a carbon atom from which a double bond originates, for example in the case of substituted lower alkenyl or lower alkynyl, tautomeric forms (resulting from keto/enol tautomerism or imine/enamine tautomerism) are possible. Those and similar tautomers the occurrence of which is familiar to a person skilled in the art are also included within the scope of the present Application. Preference is given to these compounds in which tautomerism cannot occur (e.g. where there is no bonding of —OH or —NH— to carbon atoms from which a double bond originates).

Salts of the above mentioned compounds in c) are especially acid addition salts, salts with bases or, where several salt-forming groups are present, mixed salts or internal salts, as appropriate, and are especially the pharmaceutically acceptable, non-toxic salts.

These aforementioned compounds in c) are more fully described in, for example, European Patent Publication 594 540-A1, published Apr. 27, 1994, and Canadian Patent Application 2 108 934-A1, published Apr. 24, 1994;

d) compounds found in Ghosh, A. K., et al., *J. Med. Chem.*, 36(16), 2300 (1993); Tucker, T. J., et al., *J. Med. Chem.*, 35(14), 7525 (1992); Vacca, J. P., et al., *Proc. Nat'l Acad. Sci. USA*, 91(9), 4096 (1994), especially compound L-735,524, which has the structure

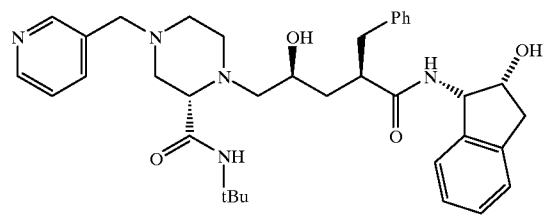

e) compounds found in Cho, S. Y., et al., *Bioorg. Med. Chem. Lett.*, 4(5), 715 (1994), and Shepard, T. A., *Bioorg. Med. Chem. Lett.*, 4(11), 1391 (1994), for example, LY-289612 and derivatives such as

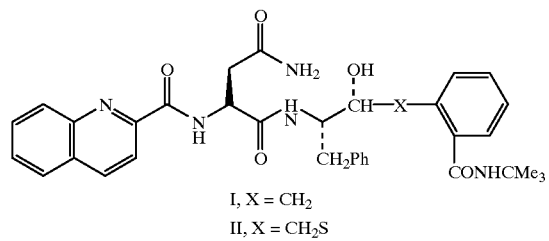

I, X = CH$_2$
II, X = CH$_2$S f) compounds found in European Patent Publication 526 009 A1, published Feb. 3, 1993 (filed as U.S. Ser. No. 07/727, 787 (Jul. 10, 1991)) and U.S. Ser. No. 07/875,908 (Apr. 29, 1992));

g) compounds, such as that of formula (L-689,502)

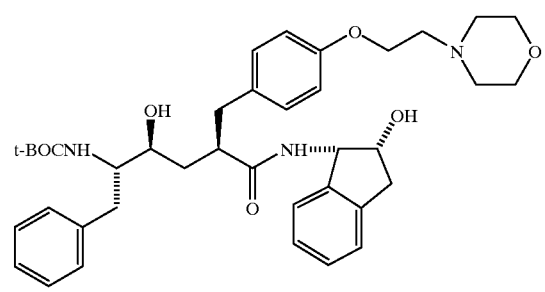

found in U.S. Pat. No. 4,661,473;

h) compounds, such as that of formula (L-694,746)

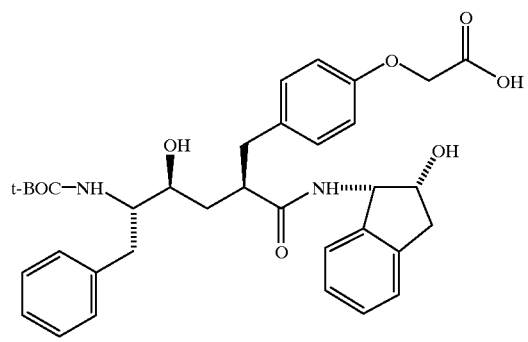

as found in U.S. Pat. No. 5,192,668;

i) compounds, such as that of formula

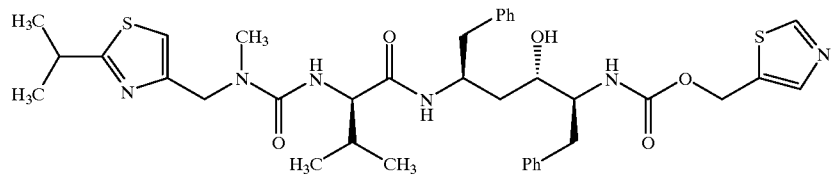

as found in International Application Publication No. WO 94/14436, published Jul. 7, 1994 (filed as U.S. Ser. No. 07/998,113, filed Dec. 29, 1992, and U.S. Ser. No. 08/158,587, filed Dec. 2, 1993); and j) compounds of the following which were presented at the 24th National Medicinal Chemistry Symposium, Salt Lake City, Utah, Jun. 21–25, 1994:

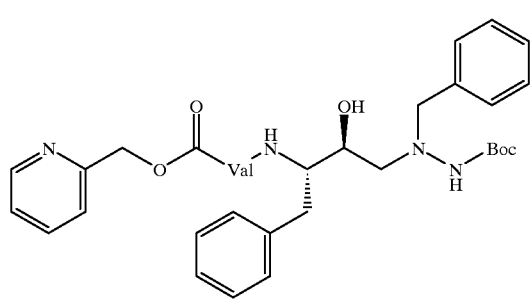

A-85883

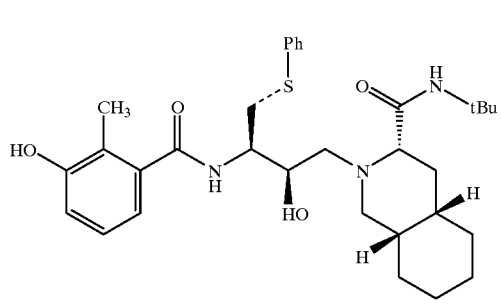

AG-1343

-continued

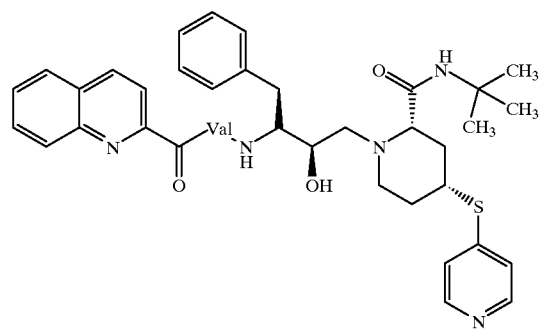

(see, also, European Patent Publication EPA 560 268-A1, published Sep. 15, 1983).

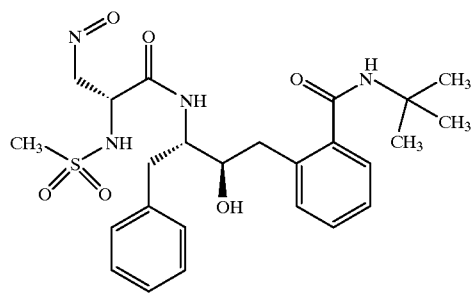

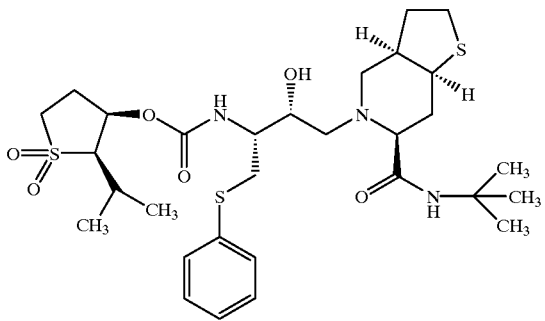

-continued

VII

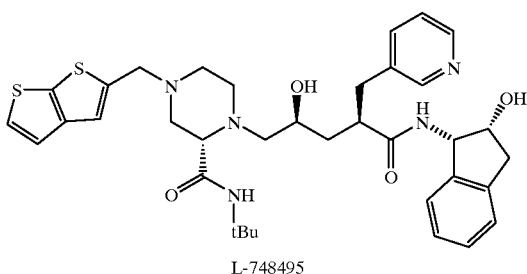

L-748495

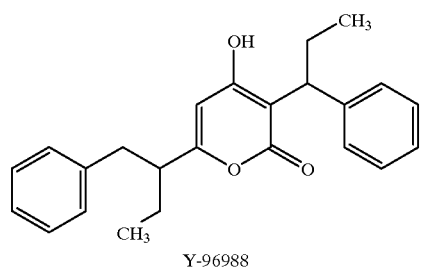

Y-96988

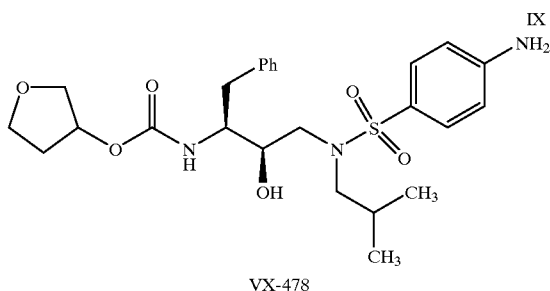

VX-478

Especially preferred is the proteinase inhibitor N-tert.-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide and its pharmaceutically acceptable salts, which is found in U.S. Pat. No. 5,196,438.

As contemplated herein, the pharmaceutically acceptable carrier comprises at least one mono-glyceride of a medium chain fatty acid and mixtures thereof. Additionally, the pharmaceutically acceptable carrier can also contain di- and triglycerides of medium chain fatty acids and mixtures thereof. The mono-, di-, and tri-glycerides also can be partially ethoxylated. More preferably, the medium chain fatty acid glycerides are selected from the group consisting of a monoglyceride of $C_8$ to $C_{10}$ medium chain fatty acids and polyethylene glycol $C_8$–$C_{10}$ medium chain fatty acid glycerides. By medium chain fatty acids, it is meant fatty acids having from about six (6) to about twelve (12) carbon atoms and preferably those having eight (8) to ten (10) carbon atoms. Examples of medium chain fatty acids include caproic (six carbon atoms), caprylic (eight carbon atoms), capric (ten carbon atoms), and lauric (twelve carbon atoms) acids.

Glycerides have the formula:

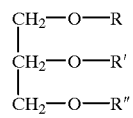

(1)

where R, R', and R" are either H or —C(O)—(CH$_2$)$_m$—CH$_3$ where m is an integer from 4 to 10 inclusive with at least one of R, R', and R" being —C(O)—(CH$_2$)$_m$—CH$_3$. In the instance where only one of R, R', and R" is —C(O)—(CH$_2$)$_m$—CH$_3$, formula (1) represents a monoglyceride. In the instance where any two of R, R', and R" are —C(O)—(CH$_2$)$_m$—CH$_3$, formula (1) represents a diglyceride. In the instance where all of R, R', and R" are —C(O)—(CH$_2$)$_m$—CH$_3$, formula (1) represents a triglyceride.

A preferable glyceride is a mixture of mono- and di-glyceride of saturated $C_8$ to $C_{10}$ (e.g., caprylic and capric) fatty acids available under the tradename CAPMUL MCM or CAPMUL MCM90, either of which contains a minimum of 70% monoglycerides, alpha, as determined by the American Oil Chemists' Society (AOCS) Test Method Cd 11–57. CAPMUL MCM90 generally contains between about 83 to about 95% monoglycerides.

CAPMUL MCM is available from Capital City Products Co., Columbus, Ohio, or Abertech, Inc. (Karlshamn), Karlshamn, Sweden. CAPMUL MCM has a maximum acid value of 2.5. Preferably, this material has an acid value of less than or equal to about 0.5. A more preferred glyceride would be CAPMUL MCM but having an acid value of less than or equal to about 0.26, further preferably less than or equal to 0.1, and most preferably less than or equal to 0.04 Another similar material is available under the tradename IMWITTOR 988 (from Hüls, Germany) (glycerol-mono-di-caprylate), which contains a minimum of 45% of monoglycerides as determined by gas chromatography. IMWITTOR 988 has a typical composition of about 50% monoglycerides, about 40% diglycerides, and about 6% triglycerides (all percentages determined by gas chromatography). IMWITTOR 988 has a maximum acid value of about 2 (in units mg KOH/g).

Acid values as used in this application are determined by AOCS Test Method Cd3a–63, acid value meaning the number of milligrams of potassium hydroxide required to neutralize the free acids in 1.0 gram of the substance. See USP XXII Chemical Tests/Fats and Fixed Oils (401).

The partially ethoxylated glyceride is preferably a liquid which is a mixture of mono-, di-, and triglycerides wherein the free hydroxy group is ethoxylated with ethylene glycol or ethylene oxide. More particularly, the partially ethoxylated glyceride is polyethylene glycol 300 $C_8$-$C_{10}$ medium chain fatty acid glyceride composition, the polyethylene glycol having an average molecular weight of from about 300 to about 500 (equivalent from about 6 to about 8 moles of ethylene oxide). Such is available under the trademark SOFTIGEN 767, available from Hüls AG or Hüls America, Piscataway, N.J. SOFTIGEN 767 is a blend of partial glycerides of natural, saturated, even numbered vegetable fatty acids with chain lengths of $C_8$ and $C_{10}$ range (greater than 90% of $C_8$ and $C_{10}$ fatty acids and less than 2% of $C_6$ and $C_{12}$ fatty acids) and has the structure(s):

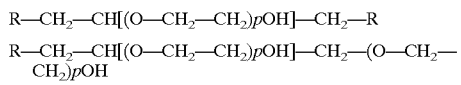

where R is $C_{8-10}$ fatty acid radicals, and p is 3 or 4.

SOFTIGEN 767 is also known by its CTFA (Cosmetics, Toiletry and Fragrance Association) name PEG-6 Caprylic/Capric Glycerides. The partially ethoxylated glyceride can also be obtained under the tradename LABRASOL (saturated polyglycolyzed $C_8$–$C_{10}$ glycerides; CTFA name PEG-8 Caprylic/Capric Glycerides) available from Gattefossé Corporation, Westwood, N.J.

Compositions which are also contemplated by this invention include formulations, with respect to the medium chain fatty acid glycerides, of about one hundred percent (100%) of mono-diglyceride of saturated $C_8$ to $C_{10}$ fatty acids (e.g, CAPMUL MCM) and zero percent (0%) of polyethylene glycol 300-caprylic/capric glyceride (e.g., SOFTIGEN 767) to about one hundred percent (100%) of polyethylene glycol 300-caprylic/capric glyceride (e.g., SOFTIGEN 767) to about zero percent (0%) of mono-diglyceride of saturated $C_8$ to $C_{10}$ fatty acids (e.g., CAPMUL MCM).

Compositions can also include PEG 400 and PEG 8000 (polyethylene glycols of molecular weights of about 400 and 8000), and polyoxyl(40) castor oil (which is castor oil with an average of 40–45 moles of ethylene oxide; also known as PEG-40 Hydrogenated Castor Oil (CFTA Name); available as Cremophor RH-40 from BASF). Cremophor RH-40 has the following typical physical properties: acid value of ≦1.0; hydroxyl value of about 60–80; and saponification of about 50–60. Certain other compositions can also contain polyoxyethylene-polyoxypropylene copolymer (a block polymer of ethylene oxide and propylene oxide).

Of the various unit dosage forms that one can contemplate, for example, hard gelatin capsules, soft gelatin capsules, tablets, caplets, enteric coated tablets, enteric coated hard gelatin capsules, enteric coated soft gelatin capsules, minicapsules, dragees, solutions, emulsions, suspensions, syrups, sprays, and suppositories, soft gelatin capsules, enteric coated soft gelatin capsules, minicapsules, and suppositories are preferred unit dosage forms and soft gelatin capsules and minicapsules are especially preferred unit dosage forms. When soft gelatin capsules are used, it is preferred that when a composition contains a polyethylene glycol, the composition of the soft gelatin capsule shell contains a humectant, for example, sorbitol, to prevent brittleness of the soft gelatin capsule.

The amount of proteinase inhibitor for the unit dosage forms, with the exception of the minicapsules, range from about 10 mg to about 3000 mg, preferably from about 25 mg to about 1800 mg, more preferably from about 25 mg to about 600 mg, even more preferably from about 50 mg to about 400 mg, and even more preferably from about 120 mg to about 300 mg, and most preferably in an amount of about 200 mg. For minicapsules, the amount of proteinase inhibitor is from about 0.5 to about 2 mg (which corresponds to a fill volume of about 5 to about 10 mg liquid). Alternatively, the size of the minicapsule can range from about 0.5 mm to about 5 mm in diameter, preferably from about 1 to about 2 mm in diameter.

For the manufacture of tablets, coated tablets, dragees and hard gelatine capsules the proteinase inhibitors can be processed with pharmaceutically inert, inorganic or organic excipients. Lactose, maize starch or derivatives thereof, talc, stearic acid or its salts etc. can be used, for example, as such excipients for tablets, dragees and hard gelatine capsules.

Suitable excipients for soft gelatine capsules are, for example, vegetable oils, waxes, fats, semi-solid and liquid polyols etc.

Suitable excipients for the manufacture of solutions and syrups are, for example, water, polyols, saccharose, invert sugar, glucose etc.

Suitable excipients for injection solutions are, for example, water, alcohols, polyols, glycerol, vegetable oils etc.

Suitable excipients for suppositories are, for example, natural or hardened oils, waxes, fats, semi-liquid or liquid polyols etc.

Moreover, the unit dose pharmaceutical compositions can contain preserving agents, solubilizers, viscosity-increasing substances, stabilizing agents, wetting agents, emulsifying agents, sweetening agents, coloring agents, flavoring agents, salts for varying the osmotic pressure, buffers, coating agents or antioxidants. Preferably, the antioxidant is dl-alpha tocopherol which is present in the inventive formulation in an amount of from about 0.01 to about 0.5% on a weight basis, preferably about 0.1% to about 0.5%. The unit dose pharmaceutical compositions can also contain still other therapeutically valuable substances.

For compositions containing from about 120 mg to about 300 mg of proteinase inhibitor, and preferably about 200 mg, the compositions can contain the materials in the following ranges (based on weight percent of the composition):

| | |
|---|---|
| $C_8$–$C_{10}$ fatty acid monoglyceride (e.g. CAPMUL MCM; or IMWITTOR 988) | 40–80% |
| dl-α-totopherol | 0.01–0.5% |
| Polyvinylpyrrolidone | 0–30% |
| PEG 400 | 0–30% |
| Polyoxyl(40) Castor Oil | 0–12% |
| PEG 8000 | 0–5% |
| Polyglycolyzed $C_8$–$C_{10}$ fatty acid glycerides (e.g. LABRASOL; or SOFTIGEN 767) | 0–10% |
| Polyoxyethylene-polyoxypropylene copolymer | 0–25% |

Preferably, for compositions containing about 200 mg of proteinase inhibitor, the compositions contain about 40–80% $C_8$–$C_{10}$ fatty acid monoglycerides, about 0.5% dl-α-tocopherol, about 0–28% PEG-400, about 0–10% Polyoxyl(40) Castor Oil; and about 0–30% polyvinylpyrroiidone. Additionally, preferred compositions are, with all containing about 200 mg of proteinase inhibitor, (a) about 0.5% dl-α-tocopherol and about 79.5% $C_8$–$C_{10}$ fatty acid monoglycerides; and (b) about 0.5% dl-α-tocopherol; about 40–76.5% $C_8$–$C_{10}$ fatty acid monoglyercides, about 0–27.5% polyoxyl(40) castor oil; and about 20–30% polyvinylpyrrolidone. More preferred compositions (mg/capsule) are as follows:

TABLE A

| Material | A23 | A24 | A25 |
|---|---|---|---|
| Proteinase Inhibitor | 200 | 200 | 200 |
| dl-α-tocopherol | 5 | 5 | 5 |
| CAPMUL MCM | 795 | 765 | 400 |
| PEG 400 | | | 275 |
| Polyoxyl(40) castor oil | | | 100 |
| Polyvinylpyrrolidone | | 30 | 20 |
| Total | 1000 | 1000 | 1000 |

The Examples below describe work conducted using N-tert.-butyl-decahydro-2-[2(R)-hydroxy-4-phenyl-3(S)-[[N-(2-quinolylcarbonyl)-L-asparaginyl]amino]butyl]-(4aS, 8aS)-isoquinoline-3(S)-carboxamide (referred to hereinbelow as "Compound A") and its pharmaceutically acceptable salts as an example of a proteinase inhibitor. Those of ordinary skill in the art also will appreciate how the invention and examples relate to those proteinase inhibitors described hereinabove and other proteinase inhibitors in general.

EXAMPLE 1

The various formulations tested below and the others which are contemplated by the present invention were made in the following manner. As an example, Formulation A-63, discussed below, was made as follows:

Compound A was sieved to remove large material.

769.0 mg of CAPMUL MCM and 1.0 mg of dl-α-tocopherol, all as liquids, were placed in a suitable vessel and were heated to 55–60° C. with continuous stirring. 30.0 mg of polyvinylpyrrolidone K30 (PVP K30; average molecular weight of about 30,000) was added to the vessel and stirred until dissolved. 200.0 mg of the sieved Compound A was added slowly to the liquid by careful sprinkling it into the liquid while vigorously stirring and maintaining the temperature of the liquid at 55–60° C.

When all of the Compound A had dissolved, the vessel was removed from the heat source, the stirring was stopped, and the resulting liquid was allowed to reach room temperature (about 20° C.). The cooled liquid was then filled into soft gel capsules.

A heating temperature of at least 55° C. was selected to prevent lengthy dissolution time of Compound A in the glyceride.

EXAMPLE 2

Inventive formulations A-23, A-24, A-59, and A-63 are set forth in Table 1 below. Formulation A-63 was prepared as described in Example 1 above. Formulations A-23, A-24, and A-59 were prepared in a manner analogous to that described in Example 1.

TABLE 1

| | mg/capsule | | | |
|---|---|---|---|---|
| MATERIAL | Formulation A-23 | Formulation A-24 | Formulation A-59 | Formulation A-63 |
| Compound A | 200.0 | 200.0 | 200.0 | 200.0 |
| CAPMUL MCM90 | 795.0 | 765.0 | 599.2 | 769.0 |
| DL-α-tocopherol | 5.0 | 5.0 | 0.8 | 1.0 |
| PVP K30 | | 30.0 | | 30.0 |
| TOTAL | 1000.0 | 1000.0 | 800.0 | 1000.0 |

EXAMPLE 3

A human volunteer study was carried out using inventive formulation A-63 as compared against noninventive formulation Formulation A-14 (Compound A-mesylate salt, 235.337 mg [equivalent to 200.000 mg of Compound A] in a carrier of anhydrous lactose, 63.300 mg; microcrystalline cellulose (Avicel PH 102), 60.000 mg; sodium starch glycolate, 16.000 mg; Povidone (polyvinylpyrrolidone) K30, 8.000 mg; and magnesium stearate, 4.000 mg; (purified water used for processing, 92.590 mg) placed in a hard gelatin capsule) to assess bioavailability.

Twelve male volunteers were used in each study, each given the equivalent of 600 mg Compound A after food: that is three capsules each of the 200 mg hard gelatin capsule Formulation A-14 and three capsules each of the 200 mg soft gelatin capsules of Formulation A-63. The 200 mg indicating that each capsule, hard or soft, contain the equivalent of 200 mg of Compound A.

After a fourteen day screening period, each subject received a single dose of either inventive formulation Formulation A-63 or non-inventive formulation Formulation A-14 within five minutes of a standardized meal (either (1) breakfast: bowl of corn flakes with 100 ml of whole milk; two rashers of bacon; two fried eggs; two slices of toast with butter; 100 ml orange juice; and 150 ml of decaffeinated coffee or tea or (2) lunch: 200 ml of soup; sandwiches made from four pieces of bread; a chocolate biscuit; an orange or apple; and 150 ml decaffeinated coffee or tea).

Blood samples were taken immediately before dosing and at 0.5, 1, 1.5, 2, 2.5, 3, 3.5, 4, 4.5, 5, 6, 7, 8, 10, 12, 16, 20, and 24 hours after the dose. After a minimum six day washout period, each volunteer received a second dose of each relevant formulation after a standardized meal and blood sampling was done at the times previously mentioned. After another minimum six day washout period, each volunteer received a second dose of each relevant formulation after a standardized meal and blood sampling was done at the times previously mentioned.

The plasma samples of Compound A in biological fluid were analyzed by solid phase sample preparation and high performance liquid chromatography with ultraviolet detector at 238 nm (HPLC/UV) as described below.

$C_8$ Advanced Automated Sample Processor (AASP) cartridges were used to extract Compound A from plasma samples. The limits of quantification were 0.5 ng/ml with 1.0 ml of plasma with a precision and accuracy of 0.5% and 99.1%, respectively.

Venous blood samples (10 ml) were taken into either glass Becton Dickinson Vacutainers or polypropylene Sarstadt monovettes containing lithium heparin as an anticoagulant, and put on ice. The samples were centrifuged within 1 hour of collection at 1500 g and the plasma transferred to 5 ml polystyrene screw top tubes and stored frozen at −20° C. Prior to transfer to the analytical laboratory, plasma samples from HIV positive patients were inactivated by heat treatment in a water bath for 2 hours at 56° C. (±1° C.) to destroy any HIV present. The samples were then refrozen at −20° C. Prior to analysis at the analytical laboratory, the samples were subjected to the same heat treatment.

A 300 μl aliquot of 0.5 molar monochloroacetic acid was added to each 1 ml aliquot of plasma, standard, or unknown and the samples were vortexed and then centrifuged for 3 minutes in a microfuge (MSE).

Using a AASP prep station (Varian, Walton on Thames, England), $C_8$ bonded phase AASP cassettes (Jones Chromatography, Hengoed, Wales) were primed with 2×1 ml of methanol and 2.×1 ml of 0.001 M ammonium acetate (pH 3) buffer. The plasma samples were then loaded onto the cassette and washed with 2×1 ml of 0.01 M ammonium acetate and 1 ml of 0.01 M ammonium acetate (pH 3) buffer:methanol (60:40). The cassettes were transferred to the AASP system and the samples eluted into the HPLC system (Kratos Spectroflow 400 pump, ABI, Warrington, England; AASP mininjector, Varian, Walton on Thames, England; LKB 2141 variable wavelength detector, Pharmacia/LKB, Milton Keynes, England).

The AASP cassettes were purged with aliquots of methanol:water:glacial acetic acid (48.8:48.8:2.4) set for 10 cycles pre-injection and 10 cycles post-injection. The valve reset time was sent to 1 minute with a typical cycle time and run time of 15 minutes.

The eluent was methanol:0.01 M ammonium acetate:glacial acetic acid (90:9.75:0.25), at a flow rate of 2 ml/min, which resulted in a back pressure of approximately 800 psi. A Phenyl Nova-Pak Guard-Pak (Waters, Harrow, England) was used with a Phenyl Nova-Pak cartridge (4 micron) (Waters, Harrow, England) fitted with in a Waters RCM 8×10 compression unit (Waters, Harrow, England). The UV detector was set at 238 nm. These conditions resulted in a retention time of about 10 minutes for Compound A. The retention time was dependent upon the analytical column (due to the number of residual silanol groups), the concentration of ammonium acetate in the mobile phase, and the amount of methanol. The optimum separation of Compound A from endogenous components was achieved with a retention time of 10 minutes, accomplished by varying the concentration of ammonium acetate used to prepare the mobile phase. The concentration of ammonium acetate was established for each analytical column and was between about 0.006 and about 0.019 M.

The peak heights of Compound A were calculated automatically by computing integrator (Maxima 820 chromatography data acquisition system, Waters, Harrow, England). Peak heights or peak height ratios versus concentrations of Compound A were used to construct linear calibration curves and calculation of subsequent patient sample concentrations using RODAS suite of programs (Roche Products Ltd., Welwyn Garden City, England). Calibration curves were established using an iteratively reweighed linear least squares regression. The time for maximum concentration ($C_{max}$), the time to achieve maximum plasma concentration $T_{max}$, and area under the plasma concentration—time profile (AUC) was determined from plasma concentration—time profile of each formulation. Statistical analyses, e.g., mean, % coefficient of variability and median were also calculated.

Relevant pharmacokinetic parameters of inventive formulation Formulation A-63 as compared to noninventive formulation Formulation A-14 are found in Table 2.

TABLE 2

| Formulation | Statistic | Parameter (units) | | | |
|---|---|---|---|---|---|
| | | $C_{max}$ (ng/mL) | $T_{max}$ (h) | tlag (h) | AUC* (ng · h/mL) |
| Formulation A-63 | Mean | 334.6 | — | — | 701.4 |
| | % CV | 70.9 | — | — | 80.9 |
| | Median | 273.6 | 1.5 | 0 | 530.1 |
| Formulation A-14 | Mean | 61.85 | — | — | 194.9 |
| | % CV | 62.3 | — | — | 59.3 |
| | Median | 57.17 | 4.5 | 0.5 | 189.9 |

*AUC calculated to the last measurable plasma concentration.

The data of Table 2 show inventive formulation Formulation A-63 shows a $C_{max}$ over five times that of noninventive Formulation A-14. Inventive formulation Formulation A-63 shows a AUC over 3.5 times that of noninventive formulation Formulation A-14. The results of this evaluation were surprising.

The Compound A-mesylate salt (used in non-inventive Formulation A-14) has a greater solubility than Compound A base (2.55 vs. 0.03 mg/ml at room temperature in water; 0.06 vs. 0.05 mg/ml at room temperature in pH 1.1 (HCl); and 2.32 vs <0.01 in pH 5.4 phosphate buffer). The mesylate salt of Compound A was used in Formulation A-14 due to its greater solubility in aqueous medium compared to Compound A base. If the Compound A base in non-inventive Formulation A-14 would have been used, the bioavailability would have been less than shown in Table 2 because of its low aqueous solubility. However, in inventive formulation Formulation A-63 which contains glycerides as a vehicle, Compound A as a free base has greater solubility than the mesylate salt of Compound A.

EXAMPLE 4

Other formulations contemplated by the present invention are as follows:

TABLE 3

| Item # | MATERIAL (mg/capsule) | Formulation A-25 | Formulation A-28 | Formulation A-29 |
|---|---|---|---|---|
| 1 | Compound A | 200.00 | 200.00 | 200.00 |
| 2 | CAPMUL MCM | 400.00 | 750.00 | 550.00 |
| 3 | PEG 400 | 275.0 | 0 | 0 |
| 4 | PEG 8000 | 0 | 49.65 | 0 |
| 5 | PEG (40) Castor Oil | 100.0 | 0 | 0 |
| 6 | Polyoxyethylene-Polyoxypropylene Copolymer | 0 | 0 | 249.65 |
| 7 | PVP 30 | 20.0 | 0 | 0 |

TABLE 3-continued

| Item # | MATERIAL (mg/capsule) | Formulation A-25 | Formulation A-28 | Formulation A-29 |
|---|---|---|---|---|
| 8 | dl-α-Tocopherol | 5.0 | 0.35 | 0.35 |
|   | Total Fill Weight (mg) | 1000.0 | 1000.0 | 1000.0 |

The formulations of Table 3 can be made in the following manner:

Mix Items 2, 3, 4, 5, 6, and 7 (where present) in a suitable vessel with stirring and warm the mixture to about 50° C. Add Compound A (item 1) to the mixture while mixing until clear solution is obtained. Then cool the mixture to room temperature. Then add dl-α-tocopherol (item 8) and mix until dissolved. Fill in size 16 oblong soft gelatin capsule.

EXAMPLE 5

Additional examples of other formulations contemplated by the present invention are as follows:

TABLE 4

| Ingredient | mg/capsule | | | |
|---|---|---|---|---|
| Compound A | 200 | 200 | 200 | 300 |
| CAPMUL MCM | 795 | 400 | 400 | 695 |
| PEG(40) Castor Oil | 0 | 120 | 0 | 0 |
| PEG 400 | 0 | 275 | 295 | 0 |
| PEG (8) caprylic/caproic glyceride | 0 | 0 | 100 | 0 |
| dl-α-tocopherol | 5 | 5 | 5 | 5 |
| TOTAL | 1000. | 1000. | 1000. | 1000. |

The formulations of Table 4 can be made in the following manner:

Mix CAPMUL MCM, and where used, PEG(40) Castor Oil, PEG 400, PEG (8) caprylic/caproic glyceride, and dl-α-tocopherol in a suitable vessel with stirring and warm the mixture to about 50° C. Add Compound A to the mixture while mixing until clear solution is obtained. Then cool the mixture to room temperature. Fill in appropriately sized hard or soft gelatin capsules. The hard gelatin capsules can be sealed to prevent any leakage of the fill material.

All publications and patent applications herein are incorporated by reference to the same extent as if each individual publication or patent application was specifically and individually indicated to be incorporated by reference.

While a number of embodiments of this invention are described herein, it is apparent that the embodiments can be altered to provide other embodiments that utilize the compositions and processes of this invention. Therefore, it will be appreciated that the scope of this invention includes all alternative embodiments and variations which are defined in the foregoing specification and by the claims appended hereto; and the invention is not to be limited by the specific embodiments that have been presented herein by way of example.

We claim:

1. A unit dose pharmaceutical composition comprising:
   (a) an effective antiviral amount of of a compound having the formula N-tert-butyl-decahydro-2-[2(R)-hydroxy-4-phenyl-3-(S)-[[N-(2-quinolylcarbonyl)-L-asparginyl]amino]butyl]-(4aS,8aS)-isoquinline-3-carboxamide, its pharmaceutically acceptable salts or esters (including their salts); and
   (b) a mixture of glycerides which is about 40 to about 80% by weight of said composition; wherein said mixture of glycerides contains at least 70% monoglycerides of $C_8$–$C_{10}$ medium chain fatty acids.

2. The composition of claim 1, wherein the weight ratio of monoglycerides in the mixture of glycerides in (b) to the effective amount of the compound in (a) is at least about 1.5.

3. The composition of claim 2, wherein the weight ratio of monoglycerides in the mixture of glycerides in (b) to the effective amount of the compound in (a) is from about 2.5 to about 3.5.

4. The composition of claim 3, wherein the mixture of glycerides in (b) has an acid value of less than about 2.5.

5. The composition of claim 4, further comprising dl-α-tocopherol.

6. The composition of claim 5, further comprising polyvinylpyrrolidone.

7. The composition of claim 1, wherein the mixture of glycerides in (b) contains about 83 to about 95% monoglycerides of $C_8$–$C_{10}$ medium chain fatty acids.

8. The composition of claim 7, wherein the weight ratio of monoglycerides in the mixture of glycerides in (b) to the effective amount of the compound in (a) is at least about 1.5.

9. The composition of claim 8, wherein the weight ratio of monoglycerides in the mixture of glycerides in (b) to the effective amount of saquinavir in (a) is from about 2.5 to about 3.5.

10. The composition of claim 9, wherein the mixture of glycerides in (b) has an acid value of less than about 2.5.

11. The composition of claim 10, further comprising dl-α-tocopherol.

12. The composition of claim 11, further comprising polyvinylpyrrolidone.

13. The composition of claim 1, wherein the effective antiviral amount of the compound in (a) is from about 50 mg to about 400 mg.

14. The composition of claim 13, wherein the weight ratio of monoglycerides in the mixture of glycerides in (b) to the effective amount of the compound in (a) is at least about 1.5.

15. The composition of claim 14, wherein the effective antiviral amount of the compound in (a) is about 200 mg.

16. The composition of claim 15, wherein the weight ratio of monoglycerides in the mixture of glycerides in (b) to the effective amount of the compound in (a) is about 3.0.

17. The composition of claim 16, further comprising about 0.01 to about 0.5% dl α-tocopherol by weight of the composition.

18. The composition of claim 17, further comprising polyvinylpyrrolidone.

19. The composition of claim 18, wherein the composition comprises about 3% polyvinylpyrrolidone by weight of the composition.

20. The composition of claim 19, wherein the dl α-tocopherol is about 0.5% by weight of the composition.

21. The composition of claim 20, wherein the mixture of glycerides in (b) is about 76.5% of the composition by weight.

22. The composition of claim 21, wherein the mixture of glycerides is CAPMULMCM.

23. The composition of claim 22, wherein the unit dose is placed in a unit dosage form selected from the group consisting of soft gelatin capsules and hard gelatin capsules.

24. The composition of claim 23, wherein the unit dosage form is a soft gelatin capsule.

25. The composition of claim 1, wherein the unit dose is placed in a unit dosage form selected from the group of soft gelatin capsules and hard gelatin capsules.

* * * * *

UNITED STATES PATENT AND TRADEMARK OFFICE
CERTIFICATE OF CORRECTION

PATENT NO. : 6,008,228
DATED : December 28, 1999
INVENTOR(S) : Bailey, et. al.

It is certified that error appears in the above-indentified patent and that said Letters Patent is hereby corrected as shown below:

COVER PAGE:

[73] Assignee: "Hoffman-La Roche Inc., Nutley, N.J." should read -- Hoffmann-La Roche Inc., Nutley, N.J. --.

-Signed and Sealed this

Fourteenth Day of November, 2000

*Attest:*

Q. TODD DICKINSON

*Attesting Officer*   *Director of Patents and Trademarks*